United States Patent
Qi et al.

(10) Patent No.: US 11,751,833 B2
(45) Date of Patent: Sep. 12, 2023

(54) TRAINING METHOD AND SYSTEM FOR COLLIMATOR BORDER DETECTION METHOD

(71) Applicants: General Electric Company, Schenectady, NY (US); Buer Qi, Beijing (CN); Dejun Wang, Beijing (CN); Wei Zhao, Beijing (CN); Huanzhong Li, Beijing (CN)

(72) Inventors: Buer Qi, Beijing (CN); Dejun Wang, Beijing (CN); Wei Zhao, Beijing (CN); Huanzhong Li, Beijing (CN)

(73) Assignee: General Electric Company, Schenectady, NY (US)

( * ) Notice: Subject to any disclaimer, the term of this patent is extended or adjusted under 35 U.S.C. 154(b) by 586 days.

(21) Appl. No.: 16/982,709

(22) PCT Filed: Mar. 22, 2019

(86) PCT No.: PCT/CN2019/079289
§ 371 (c)(1),
(2) Date: Sep. 21, 2020

(87) PCT Pub. No.: WO2019/184824
PCT Pub. Date: Oct. 3, 2019

(65) Prior Publication Data
US 2021/0059626 A1    Mar. 4, 2021

(30) Foreign Application Priority Data
Mar. 26, 2018    (CN) .......................... 201810253239.8

(51) Int. Cl.
*A61B 6/00* (2006.01)
*G06T 7/00* (2017.01)
*G21K 1/02* (2006.01)

(52) U.S. Cl.
CPC .......... *A61B 6/5205* (2013.01); *G06T 7/0012* (2013.01); *G21K 1/025* (2013.01)

(58) Field of Classification Search
CPC ..... A61B 6/5205; G06T 7/0012; G21K 1/025
See application file for complete search history.

(56) References Cited

U.S. PATENT DOCUMENTS

| | | |
|---|---|---|
| 8,135,191 B2 | 3/2012 | Rao et al. |
| 10,217,201 B2 | 2/2019 | Yan et al. |
| (Continued) | | |

FOREIGN PATENT DOCUMENTS

| | | |
|---|---|---|
| CN | 101540040 A | 9/2009 |
| CN | 103208106 A | 7/2013 |
| (Continued) | | |

OTHER PUBLICATIONS

International Search Report of the International Searching Authority for PCT/CN2019/079289 dated Jun. 25, 2019.
(Continued)

*Primary Examiner* — David P Porta
*Assistant Examiner* — Fani Polyzos Boosalis

(57) ABSTRACT

A training method (10) and system for a collimator border detection method. The training method (10) comprises the following steps: obtaining an original image acquired by an X-ray imaging system and a processed image obtained after processing the original image (11); determining on the basis of the processed image whether the processed image is a valid image (12); and extracting coordinates of a collimator border of a valid processed image, putting into a training pool the extracted coordinates of the collimator border and the original image corresponding to the valid processed image, and when the number of valid original images in the training pool reaches a preset threshold value, starting the training of the collimator border detection method (13).

20 Claims, 3 Drawing Sheets

(56) References Cited

U.S. PATENT DOCUMENTS

| | | | |
|---|---|---|---|
| 11,475,569 B2* | 10/2022 | Xu | A61B 6/06 |
| 2003/0091222 A1 | 5/2003 | Young et al. | |
| 2006/0140483 A1 | 6/2006 | Jabri et al. | |
| 2009/0238433 A1 | 9/2009 | Rao et al. | |
| 2013/0163843 A1 | 6/2013 | Park et al. | |
| 2017/0178303 A1 | 6/2017 | Yan et al. | |

FOREIGN PATENT DOCUMENTS

| | | |
|---|---|---|
| CN | 104161531 A | 11/2014 |
| CN | 106327511 A | 1/2017 |
| CN | 106911904 A | 6/2017 |
| JP | H0538334 A | 2/1993 |

OTHER PUBLICATIONS

English translation of International Search Report of the International Searching Authority for PCT/CN2019/079289 dated Jun. 25, 2019.

* cited by examiner

TRAINING METHOD AND SYSTEM FOR COLLIMATOR BORDER DETECTION METHOD

TECHNICAL FIELD

Embodiments of the present invention generally relate to the field of medical imaging, and particularly, to a training method and system for a collimator border detection method for an X-ray image.

BACKGROUND

An X-ray imaging device typically includes a collimator. Collimators are widely used in X-ray examinations to reduce patient exposure to X-ray radiation during imaging, and thus reduce the integral dose absorbed by the patient. A collimator is generally used to block invalid areas so that these areas are not irradiated by X rays. However, most X-ray images directly obtained at the X-ray imaging device are not exclusively valid throughout the image area, and may still include some invalid image areas. In view of the above, how to cut out useful image areas from X-ray images is a technical problem that urgently needs to be solved.

In light of this problem, when X-ray images are processed, the border of the collimator needs to be detected. Detecting and eliminating the border of the collimator is usually used in image enhancement and image display, and serves as important input in image enhancement and image display. There are already many methods for detecting the collimator border that exist in the art. These methods may generally be divided into two types: hardware-dependent methods and hardware-independent methods. For the hardware-dependent method, the detection method generally uses input of geometric information of the collimator to calculate the position of the collimator in an obtained image. For the hardware-independent method, it usually needs to be assumed that collimating edges of the collimator that are parallel to each other in pairs and perpendicular to each other in pairs exist in an obtained image. In practice, though, the collimator generally has a low number of collimating edges, and the collimating edges may be blocked by an imaging object. As a result, the existing collimator border detection method may still fail, which can lead to failure of later image processing and image display, and may even affect the diagnostic quality of the image.

Accordingly, there is a need to provide a training method and system for a collimator border detection method, in which the collimator border detection method can be trained according to needs, thereby optimizing the collimator border detection method.

SUMMARY

A training method for a collimator border detection method comprises the following steps: obtaining an original image acquired by an X-ray imaging system and a processed image obtained after processing the original image; determining whether the processed image is a valid image; and extracting coordinates of a collimator border of a valid processed image, putting into a training pool the extracted coordinates of the collimator border of the valid processed image and an original image corresponding to the valid processed image of which the coordinates of the collimator border are extracted, and when the number of valid original images in the training pool reaches a preset threshold, starting training of the collimator border detection method.

A computer program, wherein when the computer program runs in an X-ray imaging system, the X-ray imaging system is caused to perform the training method for a collimator border detection method described above.

A training system for a collimator border detection method comprises: an obtaining module, configured to obtain an original image acquired by an X-ray imaging system and a processed image obtained after processing the original image; a determining module, configured to determine whether the processed image is a valid image; and a training module, configured to extract coordinates of a collimator border of a valid processed image, put into a training pool the extracted coordinates of the collimator border of the valid processed image and an original image corresponding to the valid processed image of which the coordinates of the collimator border are extracted, and when the number of valid original images in the training pool reaches a preset threshold, start training of the collimator border detection method.

Other features and aspects will become clear through the following detailed description, accompanying drawings and claims.

BRIEF DESCRIPTION OF THE DRAWINGS

The present invention may be better understood by describing exemplary embodiments of the present invention with reference to accompanying drawings, in which.

DETAILED DESCRIPTION OF THE EMBODIMENTS

Figure 1:
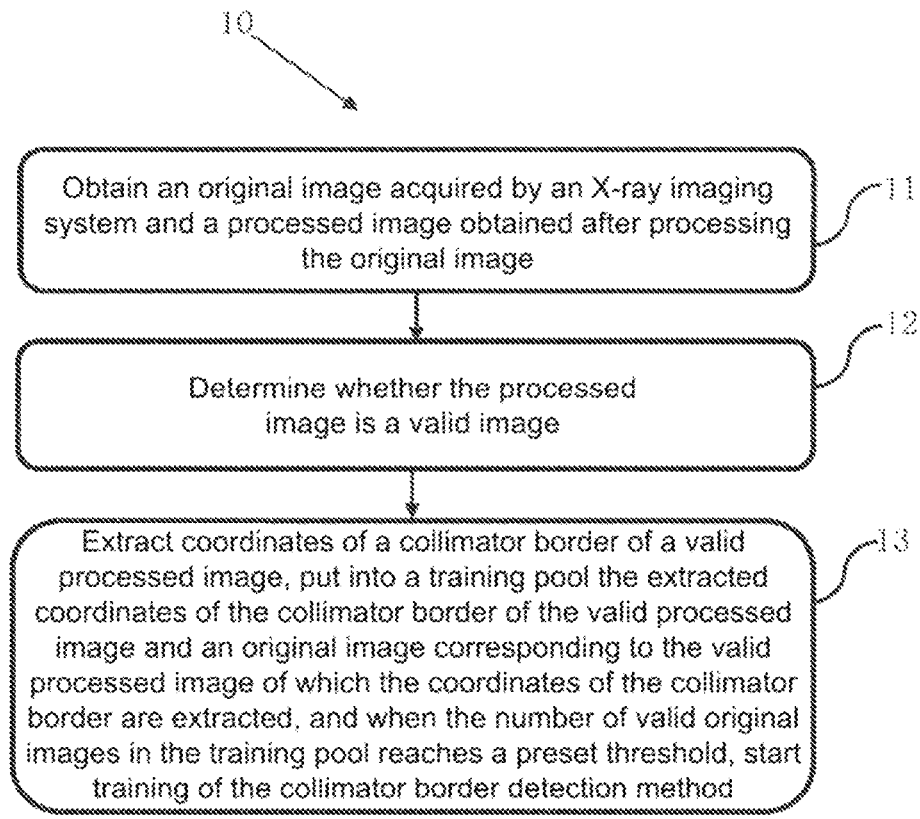
FIG. 1 is a flowchart of a training method for a collimator border detection method according to an embodiment of the present invention.

Specific implementation manners of the present invention will be described in the following. It should be noted that during the specific description of the implementation manners, it is impossible to describe all features of the actual implementation manners in detail in this description for the sake of brief description. It should be understood that in the actual implementation of any of the implementation manners, as in the process of any engineering project or design project, a variety of specific decisions are often made in order to achieve the developer's specific objectives and meet system-related or business-related restrictions, which will vary from one implementation manner to another. Moreover, it can also be understood that although the efforts made in such development process may be complex and lengthy, for those of ordinary skill in the art related to content disclosed in embodiments of the present invention, some changes in design, manufacturing, production or the like based on the technical content disclosed in the present disclosure are only conventional technical means, and should not be construed as that the content of the present disclosure is insufficient.

Unless otherwise defined, the technical or scientific terms used in the claims and the description are as they are usually understood by those of ordinary skill in the art to which the present invention pertains. The words "first," "second," "third" and similar words used in the description and claims of the patent application of the present invention do not denote any order, quantity or importance, but are merely intended to distinguish between different constituents. "One," "a(n)" and similar words are not meant to be limiting, but rather denote the presence of at least one. The word "include," "comprise" or a similar word is intended to mean that an element or article that appears before "include" or "comprise" encompasses an element or article and equivalent elements that are listed after "include" or "comprise," and does not exclude other elements or articles. The term "coupling" should also be understood in a broad sense. For example, "coupling" may be fixed connection, detachable connection, or integrated connection; may be mechanical connection, electrical connection, or mutual communication; may be direct connection or indirect connection through an intermediate medium or internal communication between two elements or interaction between two elements. Those of ordinary skill in the art can understand the specific meaning of the aforementioned terms in the present invention according to the specific situation.

The terms "module," "system," and the like are used herein to refer to a computer-related entity, for example, but not limited to, hardware, firmware, a combination of hardware and software, software, or running software configured to execute a specific operation or function. For example, the "module" and "system" may be, but not limited to, a process running on a processor, a processor, an object, an executable file, a thread of execution, a program, and/or a computer. For example, both an application running on a communication device and the communication device can be referred to as a module. One or a plurality of modules may reside in a process and/or a thread of execution, and the modules may be located in a processor or core and/or distributed between two or more processors or cores. In addition, these modules may execute from various non-transitory computer-readable media having various instructions and/or data structures stored thereon. Modules may communicate by way of local and/or remote processes, function or procedure calls, electronic signals, data packets, memory read/write, and other known computers, processors, and/or process-related communication methods.

Embodiments of the present invention provide a training method and system for a collimator border detection method, which can train the collimator border detection method through machine learning, and can optimize the collimator border detection method according to user needs and improve image processing quality. An embodiment of the present invention further provides a computer program for performing the training method for a collimator border detection method described above.

FIG. 1 is a flowchart of a training method 10 for a collimator border detection method according to an embodiment of the present invention. As shown in FIG. 1, the training method 10 for a collimator border detection method includes step 11: obtaining an original image acquired by an X-ray imaging system and a processed image obtained after processing the original image. The original image is an image directly obtained or acquired by the X-ray imaging system. The processed image generally refers to an image obtained after the X-ray imaging system processes the original image through an image processing algorithm. For example, an image obtained by subjecting the original image of the X-ray imaging system to an image processing algorithm such as edge enhancement or contrast enhancement is a processed image.

An original image and a processed image (which may be regarded as an initial processed image) with default parameter configuration can be directly obtained generally after the X-ray imaging system completes exposure. If a user is not satisfied or has other needs, parameters of the initial processed image may be generally adjusted, a new processed image is obtained after the parameters are adjusted, and then the new processed image is sent to a picture archiving and communication system for viewing and diagnosis by the user. Certainly, the user may also not perform any processing, but directly send the processed image with default parameter configuration to the picture archiving and communication system for viewing and diagnosis by the user. The processed image mentioned in the embodiment of the present invention may include the aforementioned image sent to the picture archiving and communication system with parameters manually adjusted by the user and the processed image with default parameter configuration without being manually adjusted by the user. Certainly, the processed image mentioned in the embodiment of the present invention is not limited to the two processed image types mentioned above, and may include processed images obtained by other image processing methods.

The training method 10 for a collimator border detection method shown in FIG. 1 further includes step 12: determining whether the processed image is a valid image. In step 12, a valid image in the processed image obtained by the X-ray imaging system can be judged, and then a valid original image corresponding to the processed image can be accordingly known, so that valid images can be provided for subsequent steps for use in analysis or training.

The training method 10 for a collimator border detection method further includes step 13: extracting coordinates of a collimator border of a valid processed image, putting into a training pool the extracted coordinates of the collimator border of the valid processed image and an original image corresponding to the valid processed image of which the coordinates of the collimator border are extracted, and when the number of valid original images in the training pool reaches a preset threshold, starting training of the collimator border detection method.

Figure 2:
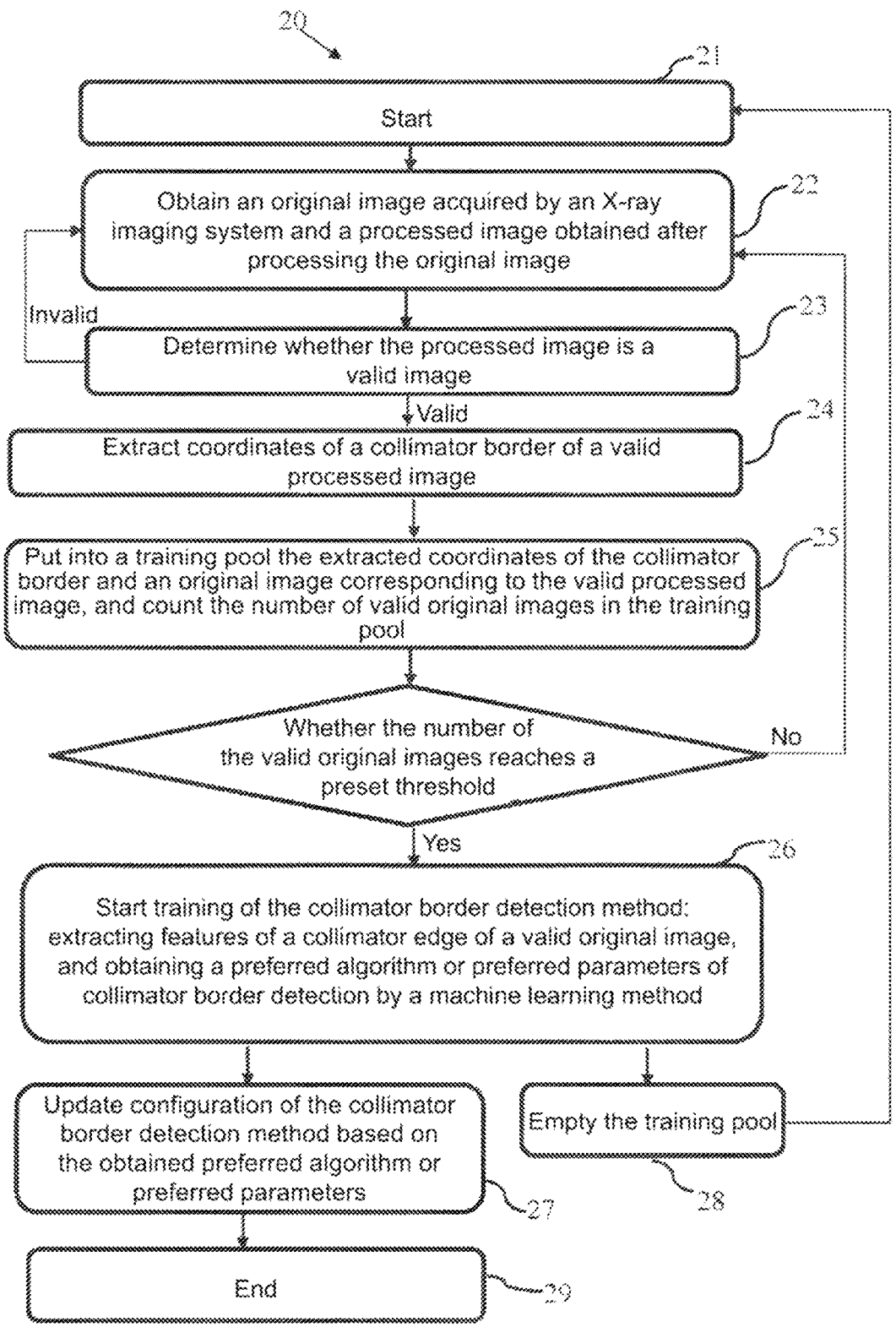
FIG. 2 is a flowchart of a training method for a collimator border detection method according to an embodiment of the present invention.

FIG. 2 is a specific flowchart of a training method 20 for a collimator border detection method according to an embodiment of the present invention. The training method 20 for a collimator border detection method includes step 21: starting. Based on step 21, training of the collimator border detection method may be started according to a user's needs or when it is considered that it is necessary to start training of the collimator border detection method.

The training method 20 for a collimator border detection method further includes step 22: obtaining an original image acquired by an X-ray imaging system and a processed image obtained after processing the original image. In step 22, an original image acquired by an X-ray imaging system and a processed image obtained through an image processing algorithm need to be obtained together.

The training method 20 for a collimator border detection method further includes step 23: determining whether the processed image is a valid image. In step 23, the processed image is mainly used for judging which images obtained by the X-ray imaging system are really valid. After step 23, it can be determined which images are valid images, and only images determined to be valid (including processed images and original images corresponding to the processed images) can be used for subsequent steps of the training method 20 for a collimator border detection method. After step 23, if the image is determined to be valid, the valid image (the processed image and the original image corresponding to the processed image) can enter the next step; if the image is determined to be invalid, the flow returns to step 22 to obtain again an original image acquired by the X-ray imaging system and a processed image obtained after processing the original image. The processed image may include images obtained through an image processing algorithm such as edge enhancement or contrast enhancement, but is not limited to these examples mentioned.

Further, in step 23, criteria for determining that the processed image is valid include that the processed image is an image sent to a picture archiving and communication system for viewing and diagnosis by the user. As long as the processed image is sent to the picture archiving and communication system, it can be considered that the processed image is a valid processed image, and the flow can enter the next step for subsequent processing.

Optionally, in step 23, the criteria for determining that the processed image is valid may further include that the image is an image sent to the picture archiving and communication system for viewing and diagnosis by the user, and the coordinates of the collimator border are directly obtained through a collimator border algorithm. That is, the border of the collimator of the image is not manually adjusted by the user, but directly obtained by the collimator border detection method. The border of the collimator is not manually adjusted by the user, so that on one hand, it indicates that directly obtaining the border of the collimator of the image through a collimator algorithm can desirably meet the user's requirements; on the other hand, it indicates that the collimator border detection method is a desirable detection method and may be used as a learning object of the training method for a collimator border detection method.

Optionally, in step 23, the criteria for determining that the processed image is valid may further include that the image is an image sent to a picture archiving and communication system for viewing and diagnosis by the user, and the coordinates of the collimator border are obtained through manual adjustment by the user. The collimator border obtained after manual adjustment by the user can usually correct false detection or missed detection of the collimator border detection method, and the user's operation habits or personal preferences can be captured, which may also serve as a learning object of the training method for a collimator border detection method.

The training method 20 for a collimator border detection method further includes step 24: extracting coordinates of a collimator border of a valid processed image. In step 24, coordinates of four vertices, for example, coordinates of an upper left vertex, coordinates of an upper right vertex, coordinates of a lower left vertex, and coordinates of a lower right vertex, of the collimator border of the valid processed image may be extracted. In step 24, other coordinates of the collimator border of the valid processed image may further be extracted, and are not limited to the coordinates of the vertices mentioned above.

The training method 20 for a collimator border detection method further includes step 25: putting into a training pool the extracted coordinates of the collimator border and an original image corresponding to the valid processed image, and counting the number of valid original images in the training pool. In step 25, the extracted coordinates of the collimator border of the valid image need to be put into the training pool, and may be used as coordinates in training of the training method 20 for a collimator border detection method. In the training process, these extracted coordinates of the collimator border may be used as training criteria or learning criteria. In addition, in step 25, an original image corresponding to the processed image that is determined to be valid needs to be put into the training pool, and may be used as a learning image of the training method 20 for a collimator border detection method.

In step 25, after the extracted coordinates of the collimator border and the original image corresponding to the valid processed image are put into the training pool, the number of valid original images in the training pool needs to be counted in real time. When the number of the valid original images in the training pool reaches a preset threshold, the flow proceeds to the next step, step 26: starting training of the collimator border detection method. If the number of the valid original images in the training pool is not greater than the preset threshold, the flow returns to step 22 to continue to obtain an original image acquired by the X-ray imaging system and a processed image. In step 25, if the number of the valid original images entering the training pool is excessively small, effective training cannot be performed. This is because sufficient learning features cannot be completed, and phenomena such as over-fitting of a training model may be caused; that is, data features of only a small number of samples are satisfied.

The preset threshold is related to a photographing part of an object to be photographed and the success rate of a collimator border detection algorithm. The preset threshold may be set to a small value for an image with low detection success rate of the collimator border detection algorithm or small amount of data in the photographing part of the photographing object. The reverse is also true: the preset threshold may be set to a large value for an image with high detection success rate of the collimator border detection algorithm or large amount of data in the photographing part of the photographing object. For example, different processing may be performed according to the photographing part of the photographing object: for a hand, the preset threshold may be set to 100; for a knee joint, the preset threshold may be set to 50. Certainly, the specific preset threshold may be adjusted according to the specific application scenario or user needs, and is not fixed.

Step 26 specifically includes: starting training of the collimator border detection method: extracting features of a collimator edge of a valid original image, and obtaining, by a machine learning method, a preferred algorithm or preferred parameters of the collimator border detection method. In step 26, the algorithm or parameters of the collimator border detection method are automatically trained by the machine learning method. The machine learning method may include a neural network algorithm, a support vector machine algorithm, deep learning, and the like. The machine learning method may employ all data in the training pool, and extract and select different features to determine the collimator border. For example, the machine learning method may extract and select features such as gray-scale features, edge features, and texture features of images in the training pool to determine the collimator border.

The training method 20 for a collimator border detection method further includes step 27: updating configuration of the collimator border detection method based on the obtained preferred algorithm or preferred parameters. In step 27, the algorithm of the collimator border detection method may be updated based on the preferred collimator border detection algorithm obtained by the machine learning method in step 26, so as to optimize the algorithm of the collimator border detection method of the X-ray imaging system. In step 27, the parameters of the collimator border detection method may also be updated based on the preferred parameters of the collimator border detection method obtained by the machine learning method in step 26, so as to optimize the collimator border detection method of the X-ray imaging system. Certainly, the algorithm and parameters of the current collimator border detection method may also be updated based on the obtained preferred algorithm and preferred parameters at the same time, so as to obtain a new optimized collimator border detection method. After the update is completed, the current training method for a collimator border detection method may proceed to the next step, step 29: ending. That is, the present or current training of the collimator border detection method ends.

If the user further needs to continue with the training of the collimator border detection method, the flow may proceed to step 28 after step 26: emptying the current training pool. After the current training pool is emptied, the flow may return to step 21 to start a next round of training of the collimator border detection method. That is, step 28 may be performed to empty the current training pool and return to step 21 to start a next round of training of the collimator border detection method.

Further, the extracted coordinates of the collimator border may be used as preferred criteria of the training method for a collimator border detection method. In some embodiments, the extracted coordinates of the collimator border may include coordinates of the collimator border directly extracted from an image sent to the picture archiving and communication system for viewing and diagnosis by the user. The coordinates of the collimator border are coordinates of the collimator border directly obtained by the collimator border detection method and are not manually adjusted by the user. In some embodiments, the extracted coordinates of the collimator border may include coordinates of the collimator border that are extracted from an image sent to the picture archiving and communication system and that are obtained after manual adjustment by the user. The aforementioned coordinates of the collimator border directly obtained by the collimator border detection method and the aforementioned coordinates of the collimator border corrected after manual adjustment by the user both can serve as training criteria or learning criteria of the training method 20 for a collimator border detection method so as to train the algorithm or parameters of the collimator border detection method.

Further, the training method 20 for a collimator border detection method further includes recording a completion time each time the training pool completes training of the collimator border detection method. In this way, the time of completing the current training of the collimator border detection method can be recorded, so as to prepare for subsequent training, prevent original images and processed images that have entered the training pool from entering the training pool again, and avoid repeated training.

Further, the training method 20 for a collimator border detection method further includes emptying the current training pool and starting a next round of training of the collimator border detection method. An image read when the next round of training of the collimator border detection method is started is a new image obtained by the X-ray imaging system after the last round of training of the collimator border detection method is completed. Whether the obtained image is a new image is determined according to a label of an acquisition time of an X-ray image. Comparison is made according to the label of the acquisition time of the X-ray image and the recorded time of completing the last training of the collimator border detection method, so that it can be judged whether the image obtained by the X-ray imaging system is a new image and has not entered the training pool.

By means of the training method for a collimator border detection method according to the embodiment of the present invention, on one hand, an algorithm or parameters of the collimator border detection method can be continuously optimized; on the other hand, preferences or operation habits of a user in manually adjusting a collimator border can be captured, and the algorithm or parameters of the collimator border detection method can also be continuously optimized, so as to meet the current application scenario or current user needs.

An embodiment of the present invention further provides a computer program, where when the computer program runs in an X-ray imaging system, the X-ray imaging system is caused to perform the training method for a collimator border detection method described above, so as to continuously optimize an algorithm or parameters of the training method for a collimator border detection method.

Figure 3:
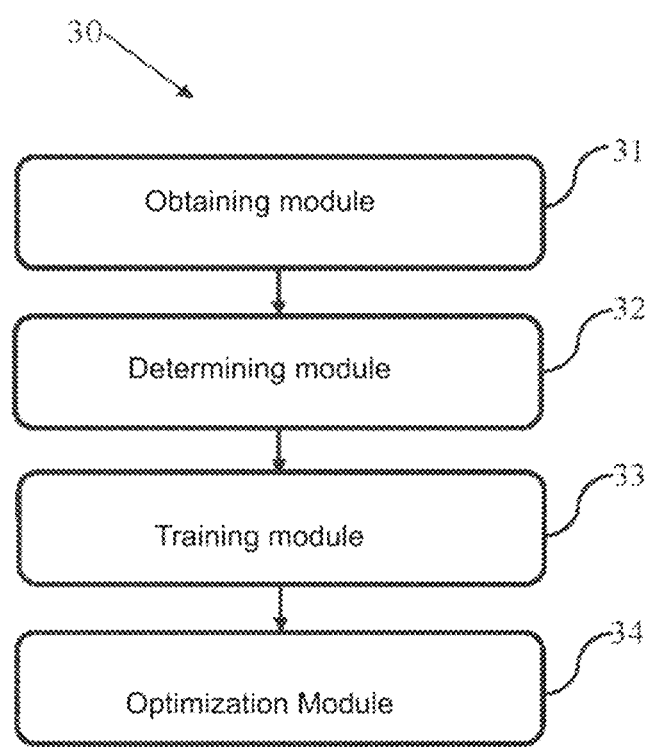
FIG. 3 is a schematic diagram of a training system for a collimator border detection method according to an embodiment of the present invention.

An embodiment of the present invention further provides a training system for a collimator border detection method. Referring to FIG. 3, FIG. 3 is a schematic block diagram of a training system 30 for a collimator border detection method according to an embodiment of the present invention. The training system 30 for a collimator border detection method includes an obtaining module 31, a determining module 32 coupled to the obtaining module 31, a training module 33 coupled to the determining module 32, and an optimization module 34 coupled to the training module 33.

The obtaining module 31 is configured to obtain an original image acquired by an X-ray imaging system and a processed image obtained after processing the original image. The processed image is used, on one hand, to determine whether the image is a valid image, and on the other hand, to extract coordinates of a collimator border. The original image is mainly used for subsequent training of the training system 30 for a collimator border detection method.

The determining module 32 is configured to determine, based on the processed image that is obtained, whether the processed image is a valid image. First criteria for the determining module 32 to determine that the processed image is valid may include that the processed image is an image sent to a picture archiving and communication system for viewing or diagnosis by a user. Second criteria for the determining module 32 to determine that the processed image is valid may include that the processed image is an image sent to a picture archiving and communication system for viewing or diagnosis by the user, and the coordinates of the collimator border in the image are obtained after manual adjustment by the user. Third criteria for the determining module 32 to determine that the processed image is valid may include that the processed image is an image sent to a picture archiving and communication system for viewing or diagnosis by the user, and the coordinates of the collimator border in the image are directly obtained by the collimator border detection method and not manually adjusted by the user. Among the aforementioned three criteria for determining that the image is valid, the first determining criteria are preferred determining criteria in the embodiment of the present invention. Certainly, the criteria for the determining module 32 to determine that the processed image is valid in the embodiment of the present invention are not limited to the aforementioned three criteria, and may also be other suitable determining criteria.

If the processed image is determined as a valid image by the determining module 32, the valid processed image and the original image corresponding to the valid processed image can enter the training module 33. If the processed image is determined as an invalid image by the determining module 32, the flow returns to the obtaining module 31 to continue to obtain an original image acquired by the X-ray imaging system and a processed image.

The training module 33 is configured to extract coordinates of a collimator border based on a processed image that is determined to be valid. The training module 33 may extract coordinates of four vertices, for example, coordinates of an upper left vertex, coordinates of an upper right vertex, coordinates of a lower left vertex, and coordinates of a lower right vertex, of the collimator border of the valid processed image. The training module 33 may further extract other coordinates of the collimator border of the valid processed image, which are not limited to the coordinates of the vertices of the collimator border mentioned above.

The training module 33 is further configured to put into a training pool the extracted coordinates of the collimator border and an original image corresponding to the valid processed image, and when the number of valid original images in the training pool reaches a preset threshold, start training of the collimator border detection method.

The training module 33 generally puts into the training pool the extracted coordinates of the collimator border and the original image corresponding to the valid processed image, and then counts the number of valid original images in the training pool in real time. Training of the collimator border detection method can be started only when the number of the valid original images in the training pool reaches a preset threshold. If the number of the valid original images in the training pool is not greater than the preset threshold, the flow returns to the obtaining unit 31 to continue to obtain an original image acquired by the X-ray imaging system and a processed image. If the number of the valid original images entering the training pool is excessively small, effective training cannot be performed. This is because sufficient learning features cannot be completed, and phenomena such as over-fitting of a training model may be caused.

The training module 33 uses the extracted coordinates of the collimator border as criteria of the training method for a collimator border detection method. In the training process, these extracted coordinates of the collimator border may be used as training criteria or learning criteria. In addition, the training module 33 puts into the training pool an original image corresponding to the processed image that is determined to be valid, which may be used as training criteria or learning criteria for training by the training system 30 for a collimator border detection method.

The training module 33 is further configured to extract features of a collimator edge of a valid original image, and obtain, by a machine learning method, a preferred algorithm or preferred parameters satisfying collimator border detection of the current user. The machine learning method may include a neural network algorithm, a support vector machine algorithm, deep learning, and the like. A machine learning method that may be employed is that, for all data in the training pool, different features need to be extracted and selected to determine the collimator border. For example, gray-scale features, edge features, texture features, and the like may be extracted and selected to determine the collimator border.

The training module 33 may extract the coordinates of the collimator border directly obtained by the collimator border detection method, or may extract the coordinates of the collimator border manually adjusted by the user. No matter which manner is adopted, the training module 33 can use the extracted coordinates of the collimator border as the criteria in the training process, so as to continuously train an algorithm or parameters of the collimator border detection method.

The training module 33 may further extract features of a collimator edge of a valid original image, and use the features in combination with the obtained coordinates of the collimator border to obtain, through continuous training and learning, a preferred algorithm or preferred parameters satisfying the collimator border detection method of the current user.

The training module 33 is further configured to record a completion time each time the training pool completes training of the collimator border detection method. In this way, the time of completing the current training of the collimator border detection method can be recorded, so as to prepare for subsequent training, prevent original images and processed images that have entered the training pool from entering the training pool again, and avoid repeated training.

The training module 33 is further configured to empty the current training pool and start a next round of training of the collimator border detection method. An image obtained by the obtaining module 33 when the training system 30 for a collimator border detection method starts the next round of training is a new image obtained by the X-ray imaging system after the last round of training of the collimator border detection method is completed. The obtaining module 31 determines whether the obtained image is a new image according to a label of an acquisition time of an X-ray image. If the label of the time of the obtained image is later than a recorded completion time of completing the last round of training of the collimator border detection method, the image is a new image and can be used in a new round of training of the collimator border detection method.

The optimization module 34 updates parameter configuration of the current collimator border detection method of the X-ray imaging system based on the preferred algorithm or preferred parameters of the collimator border detection obtained by the training module 33. The manner of the optimization module 34 optimizing the collimator border detection method may include updating the algorithm of the collimator border detection method, or updating the parameters of the collimator border detection method, or updating both the algorithm and the parameters.

By means of the training system 30 for a collimator border detection method according to the embodiment of the present invention, on one hand, an algorithm or parameters of the collimator border detection method can be continuously optimized according to user needs; on the other hand, preferences or operation habits of a user in manually adjusting a collimator border can be captured, and the algorithm or parameters of the collimator border detection method can be continuously optimized.

Some exemplary embodiments have been described above; however, it should be understood that various modifications can be made. For example, if the described techniques are performed in a different order and/or if the modules of the described system, architecture, device, or circuit are combined in different manners and/or replaced or supplemented with additional modules or equivalents thereof, a suitable result can be achieved. Accordingly, other implementation manners also fall within the protection scope of the claims.

The invention claimed is:

1. A training method for a collimator border detection method, comprising the following steps:

obtaining an original image acquired by an X-ray imaging system and a processed image obtained after processing the original image;

determining whether the processed image is a valid image; and extracting coordinates of a collimator border of a valid processed image, putting into a training pool the extracted coordinates of the collimator border of the valid processed image and an original image corresponding to the valid processed image of which the coordinates of the collimator border are extracted, and when the number of valid original images in the training pool reaches a preset threshold, starting training of the collimator border detection method.

2. The training method for a collimator border detection method according to claim 1, further comprising using the extracted coordinates of the collimator border as criteria of the training method for a collimator border detection method.

3. The training method for a collimator border detection method according to claim 1, further comprising extracting features of a collimator edge of a valid original image, and obtaining, by a machine learning method, a preferred algorithm or preferred parameters satisfying the current collimator border detection method.

4. The training method for a collimator border detection method according to claim 3, further comprising updating configuration of the current collimator border detection method based on the obtained preferred algorithm or preferred parameters of the collimator border detection method.

5. The training method for a collimator border detection method according to claim 1, wherein criteria for determining that the processed image is valid comprise that the image is an image sent to a picture archiving and communication system.

6. The training method for a collimator border detection method according to claim 1, wherein criteria for determining that the processed image is valid comprise that the image is an image sent to a picture archiving and communication system, and the coordinates of the collimator border are directly obtained through a collimator border algorithm.

7. The training method for a collimator border detection method according to claim 1, wherein criteria for determining that the processed image is valid comprise that the image is an image sent to a picture archiving and communication system, and the coordinates of the collimator border are obtained through manual adjustment by a user.

8. The training method for a collimator border detection method according to claim 1, further comprising recording a completion time each time the training pool completes training of the collimator border detection method.

9. The training method for a collimator border detection method according to claim 1, further comprising emptying the current training pool and starting a next round of training of the collimator border detection method.

10. The training method for a collimator border detection method according to claim 9, wherein an image read when the next round of training of the collimator border detection method is started is a new image obtained after the last round of training of the collimator border detection method is completed.

11. The training method for a collimator border detection method according to claim 10, wherein whether the obtained image is a new image is determined according to a label of an image acquisition time.

12. A training system for a collimator border detection method, comprising:

an obtaining module, configured to obtain an original image acquired by an X-ray imaging system and a processed image obtained after processing the original image;

a determining module, configured to determine whether the processed image is a valid image; and a training module, configured to extract coordinates of a collimator border based on a processed image that is determined to be valid, put into a training pool the extracted coordinates of the collimator border of the valid processed image and an original image corresponding to the valid processed image of which the coordinates of the collimator border are extracted, and when the number of valid original images in the training pool reaches a preset threshold, start training of the collimator border detection method.

13. The training system for a collimator border detection method according to claim 12, wherein the training module uses the extracted coordinates of the collimator border as criteria of the training method for a collimator border detection method.

14. The training system for a collimator border detection method according to claim 12, wherein the training module is further configured to extract features of a collimator edge of a valid original image, and obtain, by a machine learning method, a preferred algorithm or preferred parameters satisfying the current collimator border detection method.

15. The training system for a collimator border detection method according to claim 14, further comprising an optimization module configured to update parameter configuration of the current collimator border detection method based on the obtained preferred algorithm or preferred parameters of the collimator border detection.

16. The training system for a collimator border detection method according to claim 12, wherein criteria for the determining module to determine that the processed image is valid comprise that the image is an image sent to a picture archiving and communication system.

17. The training system for a collimator border detection method according to claim 12, wherein criteria for the determining module to determine that the processed image is valid comprise that the image is an image sent to a picture archiving and communication system, and the coordinates of the collimator border are directly obtained through a collimator border algorithm.

18. The training system for a collimator border detection method according to claim 12, wherein criteria for the image to be valid comprise that the image is an image sent to a picture archiving and communication system, and the coordinates of the collimator border are obtained through manual adjustment by a user.

19. The training system for a collimator border detection method according to claim 12, wherein the training module is further configured to record a completion time each time the training pool completes training of the collimator border detection method.

20. The training system for a collimator border detection method according to claim 12, wherein the training module is further configured to empty the current training pool and start a next round of training of the collimator border detection method.

* * * * *